US00PP12823P2

(12) United States Plant Patent
Evers

(10) Patent No.: US PP12,823 P2
(45) Date of Patent: Aug. 6, 2002

(54) ROSE PLANT NAMED 'TANFULLTAX'

(75) Inventor: Hans-Jürgen Evers, Uetersen (DE)

(73) Assignee: Rosen Tantau Mathias Tantau Nachfolger (DE)

( * ) Notice: Subject to any disclaimer, the term of this patent is extended or adjusted under 35 U.S.C. 154(b) by 0 days.

(21) Appl. No.: 09/438,194

(22) Filed: Nov. 11, 1999

(51) Int. Cl.[7] ..... A01H 5/00
(52) U.S. Cl. ..... Plt./107
(58) Field of Search ..... Plt./101, 107

(56) References Cited

PUBLICATIONS

UPOV–ROM GTITM Computer Database 2000/06, Dec. 8, 2000, GTI JOUve Retrieval Software, Citation for 'Tanfulltax'.*

*The New Royal Horticultural Society Dictionary of Gardening*, 1992, The MacMillan Press Limited, vol. 4, R to Z, page xlvi.*

* cited by examiner

*Primary Examiner*—Bruce R. Campell
*Assistant Examiner*—June Hwu
(74) *Attorney, Agent, or Firm*—Webb Ziesenheim Logdson Orkin & Hanson, P.C.

(57) ABSTRACT

The variety of rose plant having a low and spreading growth habit. The flowers are small and rounded like a small ball. The plant has very good winter hardiness, blooms repeatedly, is resistant to most diseases and is easily propagated on its own roots.

1 Drawing Sheet

BACKGROUND OF THE NEW PLANT

The present invention includes a new and distinct rose plant known by the varietal name 'Tanfulltax'.

The new plant is a spontaneous mutation (sport) of the unpatented variety "Tanotax" (German Registration No. ROS 836). The mutant was discovered by the breeder on the Tanotax plantation in Uetersen, Germany. The plant can be reproduced asexually on a rootstock of *Rosa canina*. Continued observations from the vegetative cuttings in Uetersen, Germany have confirmed that the distinguishing features of this new cultivar come true, remain stable and are retained through successive propagations.

This variety is distinguishable by its very good winter hardiness, repeated blooming, resistance to most diseases and easy propagation on its own roots. The new variety has double blossoms while 'Tanrotax' has single blossoms.

DESCRIPTION OF THE DRAWING

The accompanying photographic drawing illustrates the new cultivar at two years of outdoor growth in Northern Germany. Colors are described in reference to The Royal Horticultural Society (London) Colour Chart.

DESCRIPTION OF THE NEW PLANT

The following description sets forth the characteristics of the new cultivar.

The plant:
*Botanical name.*—*Rosa lucinda.*
*Growth habit.*—Low and spreading shrub.
Size:
*Height.*—70–80 cm.
*Width.*—Approximately 60 cm.

Habit: Low and spreading shrub.
Growth vigor: Strong.
Wood color:
*Immature.*—Green Group 138A.
*Mature.*—Greyed-Orange Group 146A.
Thorns:
*Color.*—Immature: Greyed-Purple Group 187D. Mature: Greyed-Purple Group 187A.
*Size.*—0.4 cm long.
*Shape.*—Hooked downward.
*Location on stem and branches.*—Around the stem and with a few small prickles under the leaves.
Disease resistance: Resistant to downy mildew and powdery mildew.
Hardiness: Very good in Northern Germany where mid-January temperatures can be −12° C.

FOLIAGE

Arrangement: Alternate.
Number of leaflets on typical stem leaves: 5–7.
Leaflets:
*Size.*—2.5 cm wide; 6 cm long.
*Color.*—Green Group 139A. Upper surface: Green Group 139A. Lower surface: Green Group 138A.
*Shape.*—Apex: Pointed. Base: Truncated.
*Texture.*—Leathery.
*Margin.*—Serrate.
*Petiole rachis.*—Color: Yellow-Green Group 146A with intonation of Red Group 42C. Texture: Smooth; no prickles. Stipules: Size: 0.6 cm wide; 3 cm long. Shape: Pectinate. Color: Upper surface: Yellow-Green Group 146A. Lower surface: Yellow-Green Group 146C. Texture: Smooth.

BUD

Size: 0.8 cm wide; 1.2 cm long.
Shape: Rounded.
Color: Red Group 46A opens to Red Group 53C.
Sepals:
*Color.*—Green group 139B.
*Texture.*—Covered in fine hairs.
*Apex shape.*—Pointed.
*Size.*—0.2 cm wide; 1.2 cm long.
Receptacle:
*Color.*—Green Group 137A.
*Shape.*—Funnel.
*Texture.*—Smooth.
*Size.*—0.5 cm in diameter.
Peduncle:
*Color.*—Green Group 138A with some Red Group 41D.
*Length.*—2.4 cm.
*Strength.*—Stiff.
*Texture.*—Glandular.
Foliar appendages on peduncle:
*Length.*—3.4 cm long.
*Width.*—0.5 cm wide.
*Color.*—Green Group 141A in middle and Yellow-Green Group 146A towards edge.

FLOWER

Borne (number in clusters): 7–15.
Size (diameter): 5 cm.
Form: Rounded like a small ball.
Petals:
*Number per flower.*—74–76.
*Color.*—Upper surface: Red Group 54B when half open to fully open.
Lower surface: Red Group 54B when half open to fully open. Basal spot: Red Group 49D. Color changes with maturity: Petal colors brighten at third day.
*Texture.*—Soft.
*Size.*—2 cm wide; 2.2 cm long.
*Shape.*—Overall: Lanceolate. Apex: Rounded. Base: Pointed.
*Margin.*—Entire; slightly reflexed.
*Persistence.*—Petals drop off before drying.
*Lastingness.*—About 5 days as cut flower; about 14 days as garden plant.
Petaloids: Elongated; 0.2 cm long; smooth; colored as petals.
Fragrance: None.
Blooming period: Continuously in Germany from mid-June to mid-November.

REPRODUCTIVE ORGANS

Stamens:
*Number.*—About 18.
*Anther.*—Length: 0.1 cm long. Color: Orange Group 26A.
*Filament.*—Length: 0.3 cm long. Color: Yellow-Orange, approximately Yellow-Orange Group 17D. Pollen color: Orange, approximately Orange Group 26B.
Pistils:
*Number.*—About 10.
*Style.*—Color: Green Group 136D. Length: 2 cm.
*Stigma.*—Color: Green Group 135D. Length: 2 cm.
*Hip/seed.*—None produced.

I claim:

1. A new and distinct variety of rose plant substantially as shown and described.

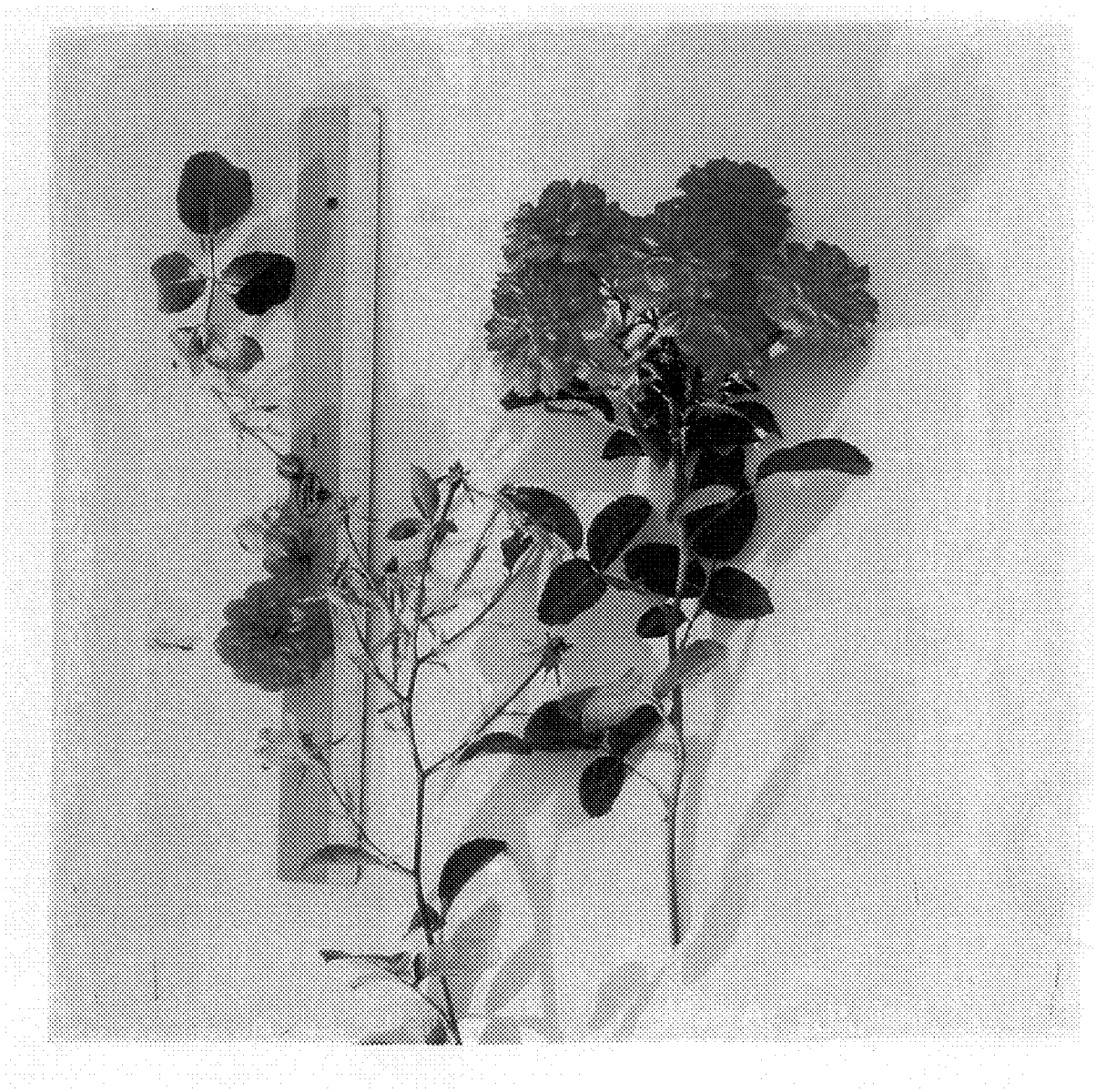

* * * * *